United States Patent
Sohn et al.

(10) Patent No.: US 9,301,056 B2
(45) Date of Patent: Mar. 29, 2016

(54) HEARING APPARATUS AND METHOD FOR MEASURING DISTANCE BETWEEN EARDRUM AND HEARING APPARATUS

(71) Applicant: Samsung Electronics Co., Ltd., Suwon-si (KR)

(72) Inventors: Jun Il Sohn, Yongin-si (KR); Jong Jin Kim, Hwaseong-si (KR); Jong Min Choi, Seoul (KR); Yun Seo Ku, Seoul (KR); Jun Whon Uhm, Anyang-si (KR); Jong Hee Han, Seoul (KR); Dong Wook Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/107,244

(22) Filed: Dec. 16, 2013

(65) Prior Publication Data
US 2014/0330160 A1    Nov. 6, 2014

(30) Foreign Application Priority Data
May 6, 2013    (KR) .................... 10-2013-0050531

(51) Int. Cl.
*H04R 25/00*    (2006.01)
*A61B 5/06*    (2006.01)

(52) U.S. Cl.
CPC .............. *H04R 25/305* (2013.01); *A61B 5/06* (2013.01); *A61B 2562/0204* (2013.01); *H04R 2225/025* (2013.01)

(58) Field of Classification Search
CPC ........ H04R 25/00; H04R 25/60; H04R 25/65; H04R 2225/49; H04R 2460/01
USPC ............................... 381/312, 316–318, 312.2
See application file for complete search history.

(56) References Cited

U.S. PATENT DOCUMENTS

| | | | |
|---|---|---|---|
| 2004/0109578 A1* | 6/2004 | Niederdrank et al. | 381/318 |
| 2011/0188692 A1 | 8/2011 | Naumann et al. | |
| 2011/0286616 A1 | 11/2011 | Beck et al. | |

FOREIGN PATENT DOCUMENTS

| | | |
|---|---|---|
| JP | 2010-022534 A | 2/2010 |
| JP | 2010-081071 A | 4/2010 |
| KR | 10-2011-0007355 A | 1/2011 |
| KR | 10-2012-0061859 A | 6/2012 |

* cited by examiner

*Primary Examiner* — Suhan Ni
(74) *Attorney, Agent, or Firm* — NSIP Law

(57) ABSTRACT

A hearing apparatus and method for measuring a distance between an eardrum and the hearing apparatus are provided. The hearing apparatus may include a signal output unit configured to output a first measurement signal, a signal identification unit configured to receive a second measurement signal, and a distance determination unit configured to determine the distance between the user's eardrum and the hearing apparatus.

22 Claims, 4 Drawing Sheets

HEARING APPARATUS AND METHOD FOR MEASURING DISTANCE BETWEEN EARDRUM AND HEARING APPARATUS

CROSS-REFERENCE TO RELATED APPLICATION(S)

This application claims the benefit under 35 USC 119(a) of Korean Patent Application No. 10-2013-0050531, filed on May 6, 2013, in the Korean Intellectual Property Office, the entire disclosure of which is incorporated herein by reference for all purposes.

BACKGROUND

1. Field

The following description relates to a hearing apparatus and method for measuring a distance between an eardrum and the hearing apparatus.

2. Description of Related Art

A hearing apparatus used to compensate the hearing of a user is typically powered using a battery. Therefore, the available power of the hearing apparatus for its usual operation of compensating hearing may be limited.

When the distance between a hearing apparatus and an eardrum is shorter, the output which is required to produce a sound of sufficient amplitude for the user to perceive is smaller. Accordingly, a hearing apparatus is typically inserted into a user's ear in order to reduce the distance between the hearing apparatus and the eardrum, thus reducing the necessary power.

However, since the shape and length of an external auditory meatus between an earflap and an eardrum is different from user to user, it is difficult to determine an insertion length of the hearing apparatus which may be appropriate for a particular user. For example, although a hearing apparatus is inserted into the ears of a first user and a second user at a same depth, the hearing apparatus may be disposed at more than an appropriate distance from the first user's eardrum while the hearing apparatus may touch the second user's eardrum.

Additionally, because the user is not able to check an insertion position of the hearing apparatus with his or her own eyes, the position of the inserted hearing apparatus may vary every time the hearing apparatus is inserted.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a hearing apparatus that modifies an audio signal collected by a microphone and outputs the modified audio signal to a user, the hearing apparatus including a signal output unit configured to output a first measurement signal; a signal identification unit configured to receive a second measurement signal; and a distance determination unit configured to determine a distance between an eardrum of the user and the hearing apparatus by comparing the first measurement signal with the second measurement signal.

The second measurement signal may be modulated from the first measurement signal in response to the first measurement signal being reflected from the eardrum; and the signal identification unit may be further configured to identify the second measurement signal from among other audio signals collected by the microphone.

The distance determination unit may be configured to determine the distance between the eardrum and the hearing apparatus using a time difference between a time at which the first measurement signal is output and a time at which the second measurement signal is received.

The distance determination unit may be configured to determine the distance between the eardrum and the hearing apparatus by comparing characteristics of the first measurement signal with characteristics of the second measurement signal.

The distance determination unit may be further configured to inform the user about a risk of damage to the eardrum in response to the distance between the eardrum and the hearing apparatus being shorter than a distance that may cause damage to the eardrum.

The distance determination unit may be further configured to inform the user that the hearing apparatus is located at a stored position, which was determined and stored by the user, in response to the distance between the eardrum and the hearing apparatus corresponding to the stored position.

The hearing apparatus may further include an audio signal modifying unit configured to modify the audio signal collected by the microphone according to auditory characteristics of the user, wherein the signal output unit is further configured to output the modified audio signal.

The audio signal modifying unit may be further configured to correct a parameter used for modifying the audio signal according to the distance between the eardrum and the hearing apparatus.

The hearing apparatus may further include a plurality of microphones; and the audio signal modifying unit may be further configured to detect a sound generation direction using the plurality of microphones, and modify the output signal using the auditory characteristics of the user corresponding to the sound generation direction.

The audio signal modifying unit may be configured to modify the audio signal collected by the microphone by amplifying the audio signal according to frequency bands corresponding to the auditory characteristics of the user.

The signal output unit may be configured to output a first output signal using a frequency not interfering with the modified audio signal.

In another general aspect, there is provided a method of operating a hearing apparatus that modifies an audio signal collected by a microphone and outputs the modified audio signal to a user, the method including outputting a first measurement signal; receiving a second measurement signal; and determining a distance between an eardrum of the user and the hearing apparatus by comparing the first measurement signal with the second measurement signal.

The second measurement signal may be modulated from the first measurement signal in response to the first measurement signal being reflected from the eardrum; and the receiving of the second measurement signal may include identifying the second measurement signal from among other audio signals collected by the microphone.

The determining may include determining the distance between the eardrum and the hearing apparatus using a time difference between a time at which the first measurement signal is output and a time at which the second measurement signal is received.

The determining may include determining the distance between the eardrum and the hearing apparatus by comparing characteristics of the first measurement signal with characteristics of the second measurement signal.

The method may further include informing the user about a risk of damage to the eardrum in response to the distance between the eardrum and the hearing apparatus being shorter than a distance that may cause damage to the eardrum.

The method may further include informing the user that the hearing apparatus is located at a stored position, which was determined and stored by the user, in response to the distance between the eardrum and the hearing apparatus corresponding to the stored position.

The method may further include modifying the audio signal collected by the microphone according to auditory characteristics of the user; and outputting the modified audio signal.

The method may further include correcting a parameter used for modifying of the audio signal according to the distance between the eardrum and the hearing apparatus.

The modifying may include detecting a sound generation direction using a plurality of microphones, and modifying the audio signal using the auditory characteristics of the user corresponding to the sound generation direction.

The modifying may include modifying the audio signal collected by the microphone by amplifying the audio signal according to frequency bands corresponding to the auditory characteristics of the user.

The outputting may include outputting a first output signal using a frequency not interfering with the modified audio signal.

In another general aspect, there is provided a hearing apparatus, including a distance determination unit configured to determine a distance between the hearing apparatus and an eardrum of a user; and an information output unit configured to output information about a position of the hearing apparatus using the determined distance.

The distance determination unit may be configured to determine the distance by comparing a first signal which is transmitted from the hearing apparatus with a second signal which is received by the hearing apparatus.

The hearing apparatus may further include an audio signal modifying unit configured to modify an audio signal according to the determined distance.

The hearing apparatus may further include a storage unit configured to store the determined distance in response to an input of the user.

Figure 1:
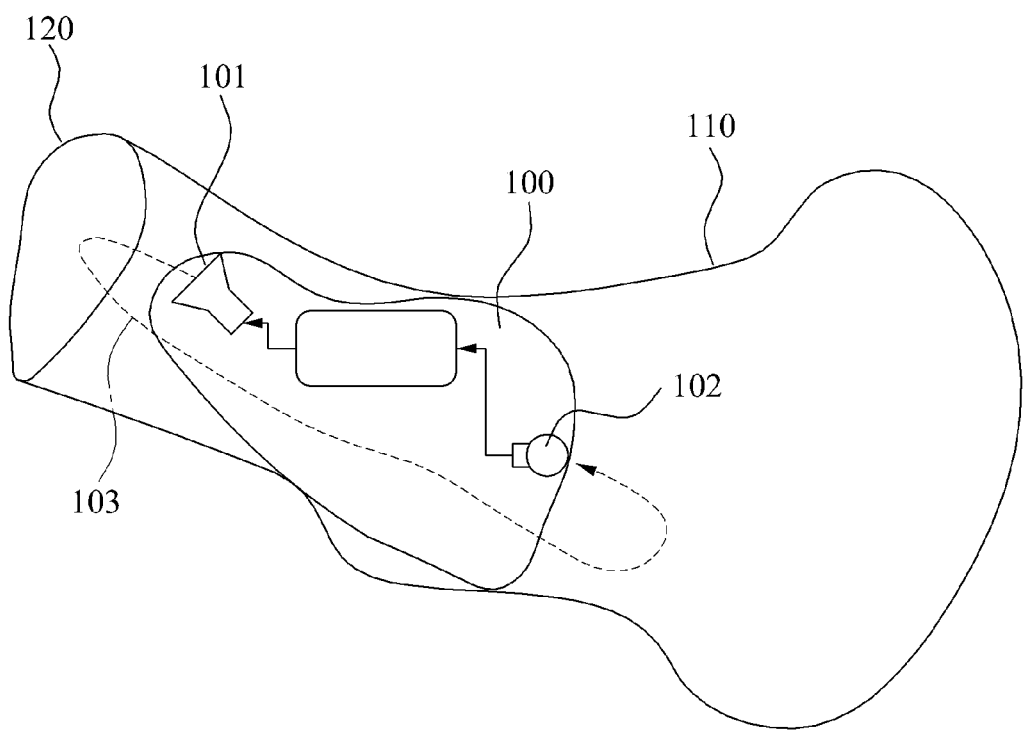
FIG. 1 is a diagram illustrating an example of a hearing apparatus, in operation, that measures a distance between an eardrum and the hearing apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 illustrates an example of a hearing apparatus 100, in operation, that measures a distance between an eardrum 120 and the hearing apparatus 100. In this example, the hearing apparatus 100 is an insertion type hearing aid configured to be inserted in a user's ear to assist the user in hearing.

For example, the hearing apparatus 100 collects audio signals around the ear and modifies the collected audio signals according to auditory characteristics of the user. Next, the hearing apparatus 100 may output the modified audio signals through a speaker 101 located adjacent to the eardrum 120, thereby providing the modified audio signals to the user.

In this example, when the hearing apparatus 100 is placed nearer to the eardrum 120, the hearing apparatus 100 may reduce the amplitude of the audio signal to be output through the speaker, thereby reducing the power consumed in outputting the audio signal. However, if the hearing apparatus 100 is placed too close to the ear drum 120, such as placing the hearing apparatus 100 in contact with the eardrum 120, the eardrum 120 may be damaged by the hearing apparatus 100.

Therefore, the hearing apparatus 100 measures the distance to the user's eardrum 120 and provides the user with the measurement result, so that the user may adjust the hearing apparatus 100 to an optimal position.

For example, the hearing apparatus 100 outputs a first measurement signal 103 for measuring the distance between the eardrum 120 and the hearing apparatus 100. The first measurement signal 103 is reflected by the eardrum 120 and transmitted to the outside of the hearing apparatus 100 through a vent formed in the hearing apparatus 100 or a space formed between the hearing apparatus 100 and the user's external auditory meatus 110. The first measurement signal 103 is modulated to a second measurement signal according to a distance between the eardrum 120 and the speaker 101 and a distance between the eardrum 120 and a microphone 102.

The microphone 102 may collect the second measurement signal transmitted around the microphone 102. The hearing apparatus 100 may compare the first measurement signal with the second measurement signal, thereby measuring the distance between the speaker 101 and the eardrum 120.

Thus, in this example, the hearing apparatus 100 measures the distance between the speaker 101 and the eardrum 120 using the speaker 101 and the microphone 102.

According to an aspect, the amplitude of the audio signal output by the hearing apparatus 100 may be varied and optimized according to the measured distance between the speaker 101 and the eardrum 120. That is, the hearing apparatus 100 may output an audio signal, which is modified according to the auditory characteristics of a user and has an optimum amplitude for its position, by measuring the distance between the speaker 101 and the eardrum 120.

Figure 2:
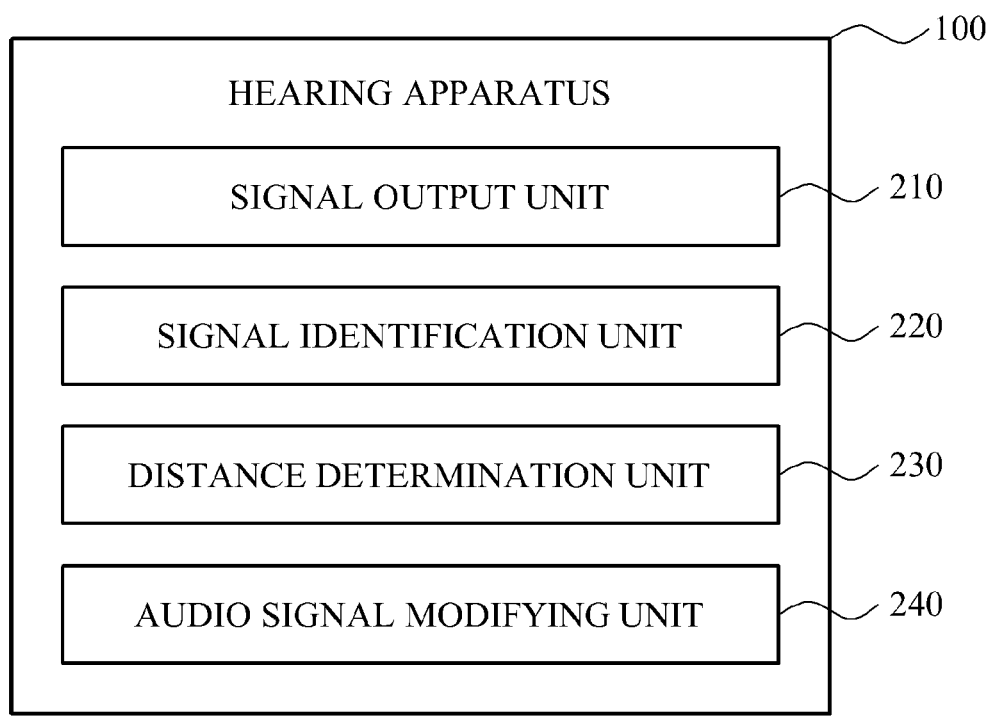
FIG. 2 is a diagram illustrating an example of the hearing apparatus.

FIG. 2 illustrates an example of the hearing apparatus 100 which measures a distance to the eardrum. Referring to FIG. 2, the hearing apparatus 100 may include a signal output unit 210, a signal identification unit 220, a distance determination unit 230, and an audio signal modifying unit 240.

In this example, the signal output unit 210 generates a first measurement signal for measuring the distance between the eardrum and the hearing apparatus 100, and output the first measurement signal.

For example, the first measurement signal may be an audio signal within an audio band or an audio signal beyond the audio band. The first measurement signal may be an audio signal having characteristics which are easily detected by the signal identification unit 220. For example, such characteristics may be maintained while the first measurement signal is modulated to a second measurement signal according to the distance between the speaker 101 and the eardrum 120 and the distance between the eardrum 120 and the microphone 102.

The signal identification unit 220 receives the second measurement signal which is modulated from the first measurement signal as the first measurement signal is reflected from the eardrum. The signal identification unit 220 may identify the second measurement signal from among all audio signals collected by the microphone 102. For example, the signal identification unit 220 searches all audio signals collected by the microphone 102 for an audio signal including the characteristics of the measurement signal, and identifies the found audio signal as the second measurement signal.

The distance determination unit 230 compares the first measurement signal generated by the signal output unit 210 with the second measurement signal identified by the signal identification unit 220, thereby determining the distance between the eardrum and the hearing apparatus 100.

For example, the distance determination unit 230 extracts characteristics for determining the distance between the eardrum 120 and the hearing apparatus 100 from the second measurement signal. These characteristics may be extracted by comparing the second measurement signal with the first measurement signal or by signal processing the second measurement signal. The distance determination unit 230 may determine the distance between the eardrum 120 and the hearing apparatus 100 using the extracted characteristics. The characteristics for determining the distance between the eardrum 120 and the hearing apparatus 100 may include at least one of a time delay between an input signal and an output signal, an amplitude change, and a difference in frequency characteristics.

For example, the distance determination unit 230 may determine the distance between the eardrum 120 and the hearing apparatus 100 using a time difference between a time at which the first measurement signal is output and a time at which the second measurement signal is received. Also, the distance determination unit 230 may determine the distance between the eardrum 120 and the hearing apparatus 100 by comparing frequency characteristics of the first measurement signal with frequency characteristics of the second measurement signal.

In addition, when the distance between the eardrum 120 and the hearing apparatus 100 is less than a distance that may cause damage to the eardrum 120, the distance determination unit 230 may provide the user with information about a risk of damage to the eardrum 120.

Also, in an example, the distance determination unit 230 may store a position of the hearing apparatus 100 as positioned by the user. For example, the distance determination unit 230 may store a current position of the hearing apparatus 100 when the user does not change the position of the hearing apparatus 100 for a period of time. In this example, the distance determination unit 230 determines whether the user changes the position of the hearing apparatus 100 based on whether the distance between the eardrum 120 and the hearing apparatus 100 has changed. Accordingly, the distance determination unit 230 may store the distance between the eardrum 120 and the hearing apparatus as the current position of the hearing apparatus 100.

In an example, when a user removes the hearing apparatus 100 from the ear or replaces the hearing apparatus 100 into the ear, the distance determination unit 230 may determine whether the distance between the eardrum 120 and the hearing apparatus 100 corresponds to a stored position. When the distance corresponds to the stored position, the distance determination unit 230 may provide the user with information indicating that the hearing apparatus 100 is located in the stored position.

According to an aspect, the user may determine a proper position of the hearing apparatus 100, and the hearing apparatus 100 may store the position determined by the user. Accordingly, when the user reinserts the hearing apparatus 100 or when the position of the hearing apparatus 100 is changed, the hearing apparatus 100 may determine a current position and inform the user of whether the current position corresponds to the stored position as previously determined by the user. Therefore, the user may control the placement of the hearing apparatus 100 in order to be in a desired position despite the position of the hearing apparatus 10 being changed or in response to the hearing apparatus 100 being newly inserted.

The audio signal modifying unit 240 may modify the audio signal collected by the microphone according to the auditory characteristics of the user. For example, the audio signal modifying unit 240 may modify or compensate the audio signal by amplifying the audio signal according to frequency bands corresponding to the auditory characteristics of a signal receiver, that is, the user. Accordingly, it should be appreciated that modifying or compensating an audio signal may include improving the sound quality of an audio signal, such as amplifying the signal, in order to meet the auditory characteristics of a user and compensate for the user's disability. Thus, the audio signal modifying unit 240 may also be referred to as an audio signal compensation unit 240.

In this example, the signal output unit 210 outputs the audio signal as modified by the audio signal modifying unit 240. Here, the signal output unit 210 may output a first output signal using a frequency not interfering with the audio signal modified by the audio signal modifying unit 240, so that the audio signal may be compensated for the user even during measurement of the distance between the eardrum 120 and the hearing apparatus 100.

The audio signal modifying unit 240 of this example corrects a parameter used for modifying the audio signal based on the distance between the eardrum and the hearing apparatus 100.

For example, the audio signal modifying unit 240 sets amplitude and/or other features for modifying the audio signal when the hearing apparatus 100 is in the position stored by the distance determination unit 230. The amplitude and other features used for modifying the audio signal may be based on the output of the audio signal at the stored position.

In addition, when the distance between the eardrum 120 and the hearing apparatus 100, as determined by the distance determination unit 230, does not correspond to the stored position, the audio signal modifying unit 240 may correct the parameters used for modifying the audio signal based on the difference between the detected current position and the stored position. In other words, the parameters may be adjusted based on the difference of the distance between the eardrum 120 and the hearing apparatus in the stored position and the detected current position. For example, when the distance between the eardrum 120 and the hearing apparatus 100 is longer than the distance of the stored position, the audio signal modifying unit 240 may correct a parameter such as gain so that the modified audio signal at the current position has the amplitude and features corresponding to the distance between the eardrum and the hearing apparatus 100 in the current position.

In addition, when the hearing apparatus 100 includes a plurality of microphones, the audio signal modifying unit 240 may detect a sound generation direction using the plurality of microphones. In this example, the audio signal modifying unit 240 compensates for sound distortion generated due to a change in a head related transfer function (HRTF) caused when the user wears the hearing apparatus 100 by compensating the sound using the auditory characteristics of the user corresponding to the sound generation direction. For example, the auditory characteristic of the user may be 3-dimensional (3D) equal loudness contour of the user which is determined by mapping hearing thresholds corresponding to directional angles and frequencies to a 2D plane constituted by a frequency and a directional angle.

Figure 3:
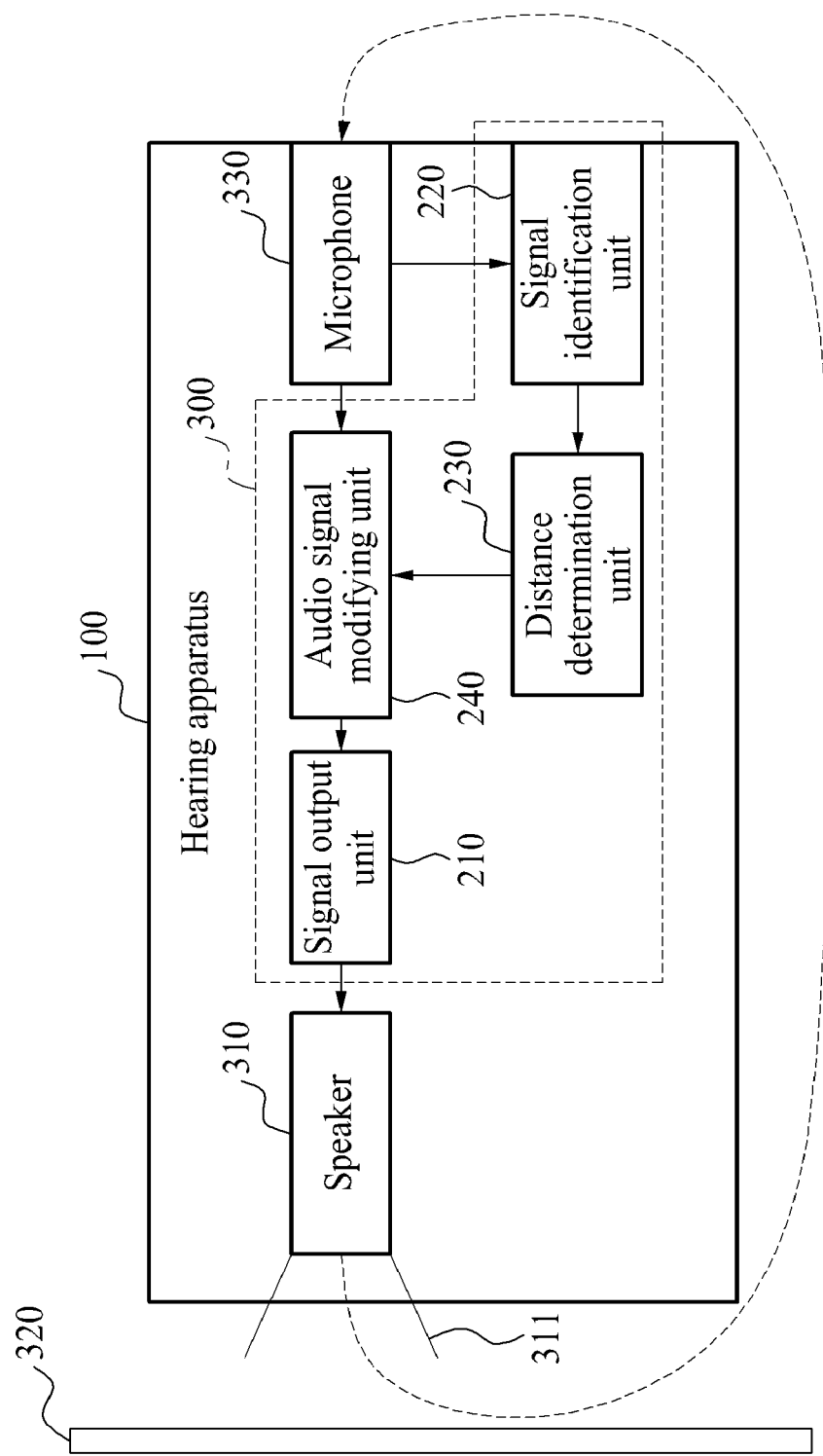
FIG. 3 is a diagram illustrating an example of operation of the hearing apparatus.

FIG. 3 illustrates an example of operation of the hearing apparatus 100.

In this example, the hearing apparatus 100 includes a distance measurement unit 300 to measure a distance between an eardrum 320 and the hearing apparatus 100, a speaker 310, and a microphone 330. In this example, the distance measurement unit 300 includes the signal output unit 210, the signal identification unit 220, the distance determination unit 230, and the audio signal modifying unit 240 as shown in FIG. 2.

The signal output unit 210 generates a first measurement signal for measuring the distance between the eardrum 320 and the hearing apparatus 100, and outputs the first measurement signal through the speaker 310. The first measurement signal may be an audio signal including characteristics which can be easily detected by the signal identification unit 220. The characteristics may be maintained while the first measurement signal is modulated to a second measurement signal according to the distance between the speaker and the eardrum 320 and the distance between the eardrum 320 and the microphone 330.

The speaker 310 outputs the first measurement signal towards the eardrum 320 of the user, and the microphone 330 collects ambient audio signals. The audio signals collected by the microphone 330 may include the second measurement signal modulated from the first measurement signal as the first measurement signal is reflected by the eardrum 320.

The microphone 330 transmits the collected audio signals to the signal identification unit 220 and the audio signal modifying unit 240. Accordingly, the signal identification unit 220 may receive the second measurement signal, and identify the signal from among the audio signals transmitted by the microphone 330. For example, the signal identification unit 220 searches for an audio signal including the characteristics of the first and second measurement signals among the audio signals transmitted by the microphone 330 to identify and find the second measurement signal.

In this example, the distance determination unit 230 determines the distance between the eardrum 320 and the hearing apparatus 100 by comparing the first measurement signal generated by the signal output unit 210 with the second measurement signal identified by the signal identification unit 220.

For example, the distance determination unit 230 extracts features for determining the distance between the eardrum 320 and the hearing apparatus 100. These features may be extracted by comparing the second measurement signal with the first measurement signal or by performing signal processing with respect to the second measurement signal. The distance determination unit 230 may determine the distance between the eardrum 320 and the hearing apparatus 100 using the extracted features. For example, the features may include at least one of a time delay between an input signal and an output signal, an amplitude change, and a difference in frequency characteristics.

Also, the distance determination unit 230 checks whether the determined distance is shorter than a distance that may cause damage to the eardrum 320. When the determined distance is shorter than the distance that may cause damage to the eardrum 320, the distance determination unit 230 may provide the user with information about the risk of damage to the eardrum 320.

Additionally, the distance determination unit 230 checks whether the determined distance corresponds to a previously stored position of the hearing apparatus 100. When the distance corresponds to the stored position, the distance determination unit 230 may provide the user with information that the hearing apparatus 100 is located at the stored position, as previously determined by the user.

In this example, the audio signal modifying unit 240 may modify the audio signal transmitted by the signal output unit 210 based on auditory characteristics of the user. The signal output unit 210 outputs the modified audio signal through the speaker 310.

Also, the audio signal modifying unit 240 may correct a parameter used for modifying the audio signal according to the distance between the eardrum 320 and the hearing apparatus 100. For example, when the distance between the eardrum 320 and the hearing apparatus 100 corresponds to the stored position, the audio signal modifying unit 240 may modify the audio signal using the parameter for modification which corresponds to the stored position.

Similarly, when the distance between the eardrum 320 and the hearing apparatus 100 does not correspond to the stored position, the audio signal modifying unit 240 may correct the parameter according to the difference between current position and the stored position, and modify the audio signal using the corrected parameter.

That is, because the hearing apparatus 100 modifies the audio signal based on the distance between the eardrum 320 and the hearing apparatus 100, the audio signal may be provided uniformly even when the position of the hearing apparatus 100 is changed.

Figure 4:
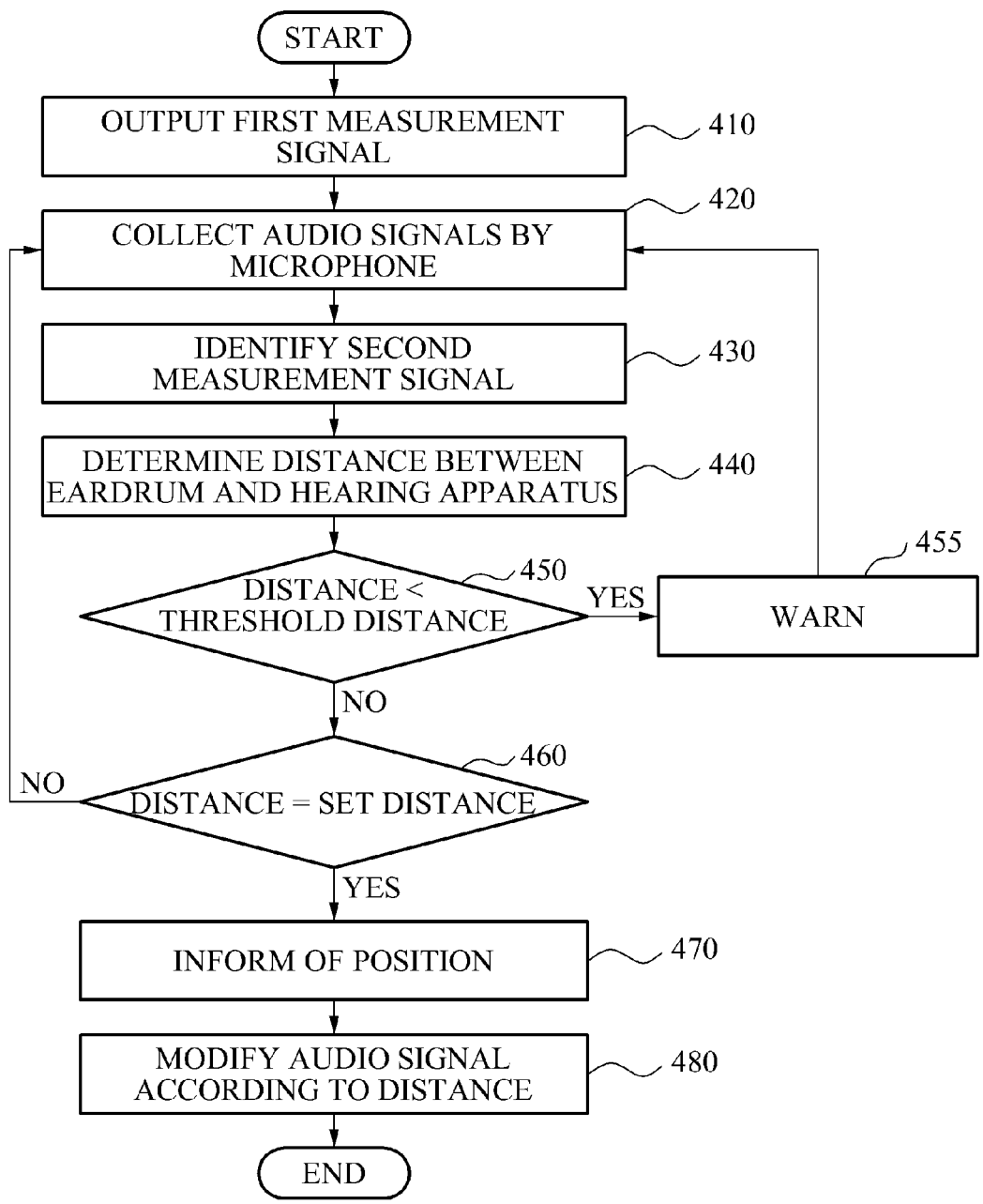
FIG. 4 is a diagram illustrating an example of a method of operating the hearing apparatus.

FIG. 4 illustrates an example of a method of operating the hearing apparatus 100.

In operation 410, a signal processing unit generates a first measurement signal for measuring the distance between an eardrum and the hearing apparatus, and output the first measurement signal. A speaker outputs the first measurement signal towards the eardrum of the user.

In operation 420, a microphone collects ambient audio signals. The audio signals collected by the microphone include the second measurement signal which is modulated from the first measurement signal output in operation 410 as the first measurement signal is reflected by the eardrum.

In operation 430, a signal identification unit identifies the second measurement signal among the audio signals collected in operation 420.

In operation 440, a distance determination unit determines the distance between the eardrum and the hearing apparatus by comparing the first measurement signal output in operation 410 with the second measurement identified in operation 430.

In an example, the distance determination unit may extract features for determining the distance between the eardrum and the hearing apparatus. These features may be extracted by comparing the second measurement signal with the first measurement signal or by performing signal processing with respect to the second measurement. Next, the distance determination unit determines the distance between the eardrum and the hearing apparatus using the extracted features. For example, the features may include at least one of a time delay between an input signal and an output signal, an amplitude change, and a difference in frequency characteristics.

In operation 450, the distance determination unit checks whether the distance between the eardrum and the hearing apparatus determined in operation 440 is shorter than a threshold distance that may cause damage to the eardrum. When the determined distance is shorter than the threshold distance, the distance determination unit may perform operation 455.

In operation 455, the distance determination unit warns the user of a risk of damage the eardrum from the hearing apparatus. For example, the distance determination unit 230 may output a sound or visual warning of the risk.

In operation 460, the distance determination unit checks whether the distance between the eardrum and the hearing apparatus as determined in operation 440 is equal to a set distance. This set distance may be a distance from a position of the hearing apparatus to the eardrum as previously determined by the user and stored by the distance determination unit.

When the distance between the eardrum and the hearing apparatus is not equal to the set distance, the distance determination unit may end the operation and the microphone may perform operation 420. When the distance between the eardrum and the hearing apparatus is equal to the set distance, the distance determination unit may perform operation 470.

In operation 470, the distance determination unit provides information that the hearing apparatus is located in the position determined by the user.

In operation 480, the audio signal modifying unit may modify the audio signal collected by the microphone in operation 420 according to the auditory characteristics of the user. In this example, the signal output unit outputs the audio signal modified by the audio signal modifying unit through the speaker.

In this example, the audio signal modifying unit corrects a parameter used for compensation of the audio signal according to the distance between the eardrum and the hearing apparatus, determined in operation 440.

For example, the audio signal modifying unit may set amplitude and features of the modified audio signal based on the output of the audio signal at the position stored by the distance determination unit. In addition, when the distance between the eardrum and the hearing apparatus does not correspond to the stored position, the audio signal modifying unit may correct the parameter used for modifying of the audio signal, according to the difference between the current position and the stored position. For example, when the distance between the eardrum and the hearing apparatus in a current position is longer than a distance between the eardrum and the hearing apparatus in the stored position, the audio signal modifying unit may correct a parameter such as gain so that the modified audio signal has the amplitude and features corresponding to the distance between the eardrum and the hearing apparatus in the current position.

For example, the hearing apparatus may include an information output unit which outputs information about the distance between the user's eardrum and the hearing apparatus. The information output unit may output a sound or a visual which informs the user of the position of the hearing apparatus. The information output unit may also be wirelessly connected to an external display for outputting the information on the display. Additionally, the information output unit may be connected to an indicator which indicates to the user how the hearing apparatus should be moved in order to match an optimal or previously stored position.

The various units, modules, elements, and methods, such as the speaker 101, microphone 102, signal output unit 210, signal identification unit 220, distance determination unit 230, and audio signal modifying unit 240, described above may be implemented using one or more hardware components, one or more software components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

Although specific terminology has been used in this disclosure, for example, audio signal modifying unit 240, it will be apparent to one of ordinary skill in the art that different terminology may be used to describe the same features, for example, audio signal compensation unit 240, and such different terminology may appear in other applications.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A hearing apparatus that modifies an audio signal collected by at least one microphone and outputs the modified audio signal to a user, the hearing apparatus comprising:
   a signal output unit configured to generate and output a first measurement signal;
   a signal identification unit configured to receive a second measurement signal defining a reflection of the first measurement signal; and
   a distance determination unit configured to determine a distance between an eardrum of the user and the hearing apparatus by comparing the first measurement signal with the second measurement signal.

2. The hearing apparatus of claim 1, wherein
   the second measurement signal is modulated from the first measurement signal in response to the first measurement signal being reflected from the eardrum; and
   the signal identification unit is further configured to identify the second measurement signal from among other audio signals collected by the at least one microphone.

3. The hearing apparatus of claim 1, wherein the distance determination unit is configured to determine the distance between the eardrum and the hearing apparatus using a time difference between a time at which the first measurement signal is output and a time at which the second measurement signal is received.

4. The hearing apparatus of claim 1, wherein the distance determination unit is configured to determine the distance between the eardrum and the hearing apparatus by comparing characteristics of the first measurement signal with characteristics of the second measurement signal.

5. The hearing apparatus of claim 1, wherein the distance determination unit is further configured to inform the user about a risk of damage to the eardrum in response to the distance between the eardrum and the hearing apparatus being shorter than a distance that may cause damage to the eardrum.

6. The hearing apparatus of claim 1, wherein the distance determination unit is further configured to inform the user that the hearing apparatus is located at a stored position, which was determined and stored by the user, in response to the distance between the eardrum and the hearing apparatus corresponding to the stored position.

7. The hearing apparatus of claim 1, further comprising:
an audio signal modifying unit configured to modify the audio signal collected by the at least one microphone according to auditory characteristics of the user,
wherein the signal output unit is further configured to output the modified audio signal.

8. The hearing apparatus of claim 7, wherein the audio signal modifying unit is further configured to correct a parameter used for modifying the audio signal according to the distance between the eardrum and the hearing apparatus.

9. The hearing apparatus of claim 7, wherein
the audio signal modifying unit is further configured to detect a sound generation direction using the at least one microphone, and modify the output signal using the auditory characteristics of the user corresponding to the sound generation direction.

10. The hearing apparatus of claim 7, wherein the audio signal modifying unit is configured to modify the audio signal collected by the at least one microphone by amplifying the audio signal according to frequency bands corresponding to the auditory characteristics of the user.

11. The hearing apparatus of claim 7, wherein the signal output unit is configured to output a first output signal using a frequency not interfering with the modified audio signal.

12. A method of operating a hearing apparatus that modifies an audio signal collected by at least one microphone and outputs the modified audio signal to a user, the method comprising:
generating and outputting a first measurement signal;
receiving a second measurement signal defining a reflection of the first measurement signal; and
determining a distance between an eardrum of the user and the hearing apparatus by comparing the first measurement signal with the second measurement signal.

13. The method of claim 12, wherein
the second measurement signal is modulated from the first measurement signal in response to the first measurement signal being reflected from the eardrum; and
the receiving of the second measurement signal comprises identifying the second measurement signal from among other audio signals collected by the at least one microphone.

14. The method of claim 12, wherein the determining comprises determining the distance between the eardrum and the hearing apparatus using a time difference between a time at which the first measurement signal is output and a time at which the second measurement signal is received.

15. The method of claim 12, wherein the determining comprises determining the distance between the eardrum and the hearing apparatus by comparing characteristics of the first measurement signal with characteristics of the second measurement signal.

16. The method of claim 12, further comprising:
informing the user about a risk of damage to the eardrum in response to the distance between the eardrum and the hearing apparatus being shorter than a distance that may cause damage to the eardrum.

17. The method of claim 12, further comprising:
informing the user that the hearing apparatus is located at a stored position, which was determined and stored by the user, in response to the distance between the eardrum and the hearing apparatus corresponding to the stored position.

18. The method of claim 12, further comprising:
modifying the audio signal collected by the at least one microphone according to auditory characteristics of the user; and
outputting the modified audio signal.

19. The method of claim 18, further comprising:
correcting a parameter used for modifying of the audio signal according to the distance between the eardrum and the hearing apparatus.

20. The method of claim 18, wherein the modifying comprises detecting a sound generation direction using the at least one microphone, and modifying the audio signal using the auditory characteristics of the user corresponding to the sound generation direction.

21. The method of claim 18, wherein the modifying comprises modifying the audio signal collected by the at least one microphone by amplifying the audio signal according to frequency bands corresponding to the auditory characteristics of the user.

22. The method of claim 18, wherein the outputting comprises outputting a first output signal using a frequency not interfering with the modified audio signal.

* * * * *